United States Patent
Imaizumi et al.

(10) Patent No.: US 8,974,378 B2
(45) Date of Patent: Mar. 10, 2015

(54) SCANNING ENDOSCOPE APPARATUS

(71) Applicant: Olympus Medical Systems Corp., Tokyo (JP)

(72) Inventors: Katsuichi Imaizumi, Hino (JP); Tetsuhide Takeyama, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/178,829

(22) Filed: Feb. 12, 2014

(65) Prior Publication Data

US 2014/0194691 A1 Jul. 10, 2014

Related U.S. Application Data

(63) Continuation of application No. PCT/JP2013/062700, filed on May 1, 2013.

(30) Foreign Application Priority Data

Aug. 7, 2012 (JP) ................................. 2012-175244

(51) Int. Cl.
  *A61B 1/04* (2006.01)
  *A61B 1/06* (2006.01)
  *A61B 1/00* (2006.01)
(52) U.S. Cl.
  CPC ......... *A61B 1/00172* (2013.01); *A61B 1/00009* (2013.01); *A61B 1/0005* (2013.01); *A61B 1/0676* (2013.01)
  USPC ............ 600/178; 600/103; 600/160; 600/182
(58) Field of Classification Search
  CPC .... A61B 1/00172; A61B 1/07; A61B 5/0062; A61B 5/0066
  USPC .......................... 600/103, 109, 160, 178, 182
  See application file for complete search history.

(56) References Cited

U.S. PATENT DOCUMENTS

| | | | |
|---|---|---|---|
| 5,309,895 A | 5/1994 | Yabe | |
| 6,485,413 B1* | 11/2002 | Boppart et al. | 600/160 |
| 6,950,692 B2* | 9/2005 | Gelikonov et al. | 600/473 |
| 7,604,590 B2* | 10/2009 | Tokuda et al. | 600/129 |
| 2008/0161648 A1 | 7/2008 | Karasawa | |
| 2008/0243031 A1* | 10/2008 | Seibel et al. | 600/566 |

(Continued)

FOREIGN PATENT DOCUMENTS

| | | |
|---|---|---|
| JP | 05-095899 A | 4/1993 |
| JP | 2008-165236 A | 7/2008 |

(Continued)

*Primary Examiner* — John P Leubecker
(74) *Attorney, Agent, or Firm* — Scully, Scott, Murphy & Presser, PC

(57) ABSTRACT

A scanning endoscope apparatus includes a light source section that emits illumination light, an optical fiber that irradiates the illumination light from a distal end to a subject with directivity, a drive element and a scanning drive section that perform scanning by the distal end of the optical fiber, a first light detection section that detects light from a direction of the distal end of the optical fiber, a second light detection section that detects light from an entire scanning range, and an image processing section that forms image information to be outputted to a display section based on a result of addition of a detection result corresponding to an external factor light component in a first light detection result and a second light detection result.

5 Claims, 6 Drawing Sheets

(56) References Cited

U.S. PATENT DOCUMENTS

| | | | |
|---|---|---|---|
| 2008/0281207 A1* | 11/2008 | Johnston | 600/476 |
| 2009/0137893 A1* | 5/2009 | Seibel et al. | 600/407 |
| 2009/0244260 A1* | 10/2009 | Takahashi et al. | 348/45 |
| 2010/0121146 A1 | 5/2010 | Sugimoto | |
| 2012/0041290 A1* | 2/2012 | Perelman | 600/326 |
| 2012/0241620 A1* | 9/2012 | On | 250/338.1 |
| 2013/0182261 A1* | 7/2013 | Hirota | 356/479 |
| 2013/0345510 A1* | 12/2013 | Hadani | 600/113 |

FOREIGN PATENT DOCUMENTS

| | | |
|---|---|---|
| JP | 2010-117442 A | 5/2010 |
| JP | 2011-041754 A | 3/2011 |
| JP | 2011-055939 A | 3/2011 |

* cited by examiner

SCANNING ENDOSCOPE APPARATUS

CROSS REFERENCE TO RELATED APPLICATION

This application is a continuation application of PCT/JP2013/062700 filed on May 1, 2013 and claims benefit of Japanese Application No. 2012-175244 filed in Japan on Aug. 7, 2012, the entire contents of which are incorporated herein by this reference.

BACKGROUND OF THE INVENTION

1. Field of the Invention

The present invention relates to a scanning endoscope apparatus that acquires an image of a subject by scanning of illumination light having directivity.

2. Description of the Related Art

There has been proposed a scanning endoscope apparatus that acquires an image of a subject by irradiating illumination light to the subject with directivity and receiving reflected light while performing scanning in a direction of the illumination light.

For example, in a technique described in Japanese Patent Application Laid-Open Publication No. 2008-165236, an actuator is provided at a distal end portion of an endoscope and a distal end portion (12P) of an optical fiber is vibrated in a spiral manner. Further, a light refraction portion (12T) is provided in the optical fiber (12) behind the actuator (16) and slope surfaces (12X, 12Y) are formed on a cladding (12B). Further, a plurality of photo sensors (14) are provided around the optical fiber (12) behind the light refraction portion (12T), and a resin (19) having refractive index higher than that of the cladding (12B) is filled between the photo sensors (14) and the actuator (16). The reflected light that progresses in the cladding 12B exits from the slope surface (12X) and is made incident to the photo sensor (14). It is stated to thereby transmit light with high accuracy and to acquire information on an object by a simple construction.

In a technique described in Japanese Patent Application Laid-Open Publication No. 2011-55939, in an endoscope apparatus in which a probe (15) of a scanning endoscope is insertable into a forceps channel (10F) of a video scope (10), when a diagnostic mode is set, a normal observation image which is a full-color image and a fluorescence observation image are generated by alternately irradiating white light and excitation light, and a protruding length of a distal end portion (15T) of the probe and a bending angle (ω) of a distal end portion (10T) of an endoscope are detected. Based on the detected protruding length and the bending angle, an enlargement/reduction scale factor of a fluorescence observation image and an amount of phase shift are determined, and in a synthesis switching circuit (36) enlargement/reduction processing of the fluorescence observation image is performed in accordance with the determined scale factor so that a size of an observation subject such as an affected area coincides with a size of the observation subject in the normal observation image, and then phase shift processing is performed in accordance with the determined amount of phase shift. It is stated to thereby obtain a misalignment-free synthetic image between two images in the endoscope apparatus in which the probe can be used.

Further, in a technique described in Japanese Patent Application Laid-Open Publication No. 2010-117443, a scanning endoscope has a light supply fiber (53), a fiber drive section (54), and a top optical unit (60). The light supply fiber (53) emits light from an emitting end. The fiber drive section (54) bends the light supply fiber (53) from a first line (L1). The top optical unit (60) has first and second mirrors (61, 62). The first mirror (61) reflects light emitted from the light supply fiber (53) to the second mirror (62). The second mirror (62) reflects light reflected by the first mirror (61) in a direction including the first direction as a positive vector and going toward a point on the first straight line (L1). It is stated to thereby reduce distortion of an image in the vicinity of a center of spiral in a fiber-optic scanning endoscope which performs spiral type scanning In the scanning endoscopes as described above, it is configured that a direction of a light emission end of the optical fiber which conducts the illumination light is changeable and the scanning of the illumination light is performed by changing the direction of the light emission end of the optical fiber as time elapses. On the other hand, the configuration for receiving light from a subject is made such that all the light from a scanning range of the illumination light can be received.

Accordingly, information indicating in which direction the received light comes (i.e. from which part of the subject the light comes) is not included in a signal generated by the received light. Therefore, configuration of an endoscopic image is performed by assuming that the received light is the return light from a part of the subject which is irradiated with the emitted light.

With the configuration of the conventional scanning endoscope apparatus as described above, an image of the subject can be precisely formed when there is not any external factor light (which is not return light of the illumination light emitted from the optical fiber, e.g. light generated by a treatment instrument for performing treatment on a subject with light emission, such as an electric knife and a medical laser) other than the return light from the subject within a light receiving range.

SUMMARY OF THE INVENTION

A scanning endoscope apparatus according to an aspect of the present invention includes: a light source section that emits illumination light; a light conducting section that conducts the illumination light and irradiates the illumination light from a distal end to a subject with directivity; a scanning section that performs scanning by changing a direction of the distal end of the light conducting section; a first light detection section that detects light from the subject in the direction of the distal end of the light conducting section; a second light detection section that detects light from a scanning range of the distal end of the light conducting section by the scanning section with directivity which is broader than directivity of the first light detection section; an image processing section that performs addition processing on a detection result corresponding to an external factor light component in a detection result by the first light detection section and a detection result by the second light detection section, and forms image information to be outputted to a display section, which displays an image, based on a result of the addition processing.

DETAILED DESCRIPTION OF THE PREFERRED EMBODIMENTS

Figure 1:
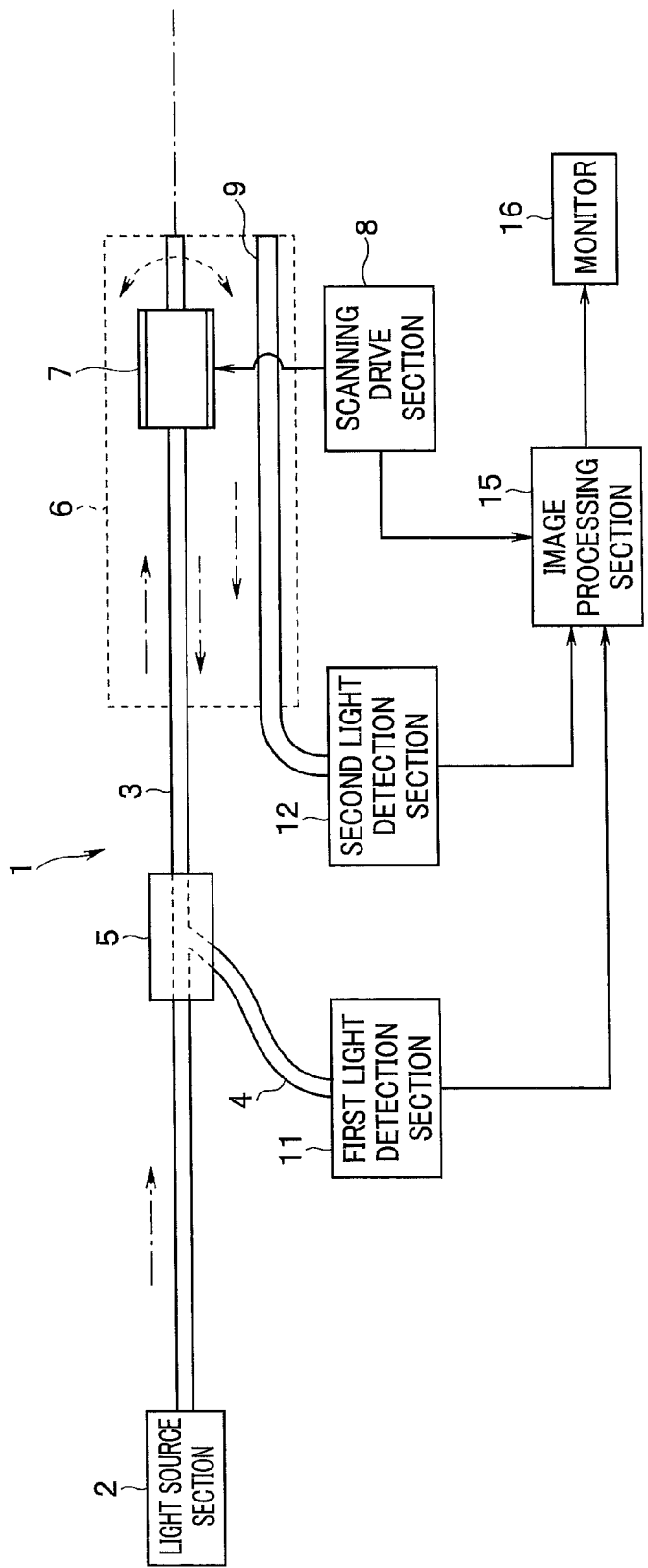
FIG. 1 is a diagram showing a configuration example of a scanning endoscope apparatus in embodiment 1 of the present invention.

Hereinafter, embodiments of the present invention will be described referring to the drawings.

[Embodiment 1]

FIG. 1 to FIG. 7 show embodiment 1 of the present invention, and FIG. 1 is a diagram showing a configuration example of a scanning endoscope apparatus.

A scanning endoscope apparatus 1 shown in FIG. 1 comprises a light source section 2, an optical fiber 3, a branch optical fiber 4, an optical coupler 5, an endoscope 6, a drive element 7, a scanning drive section 8, an optical fiber bundle 9, a first light detection section 11, a second light detection section 12, an image processing section 15, and a monitor 16.

The light source section 2 emits illumination light, and is configured to emit color illumination light including, for example, illumination light of a plurality of colors, specifically, a red light emission laser which emits red (R) narrow band light, a green light emission laser which emits green (G) narrow band light, and a blue light emission laser which emits blue (B) narrow band light. Here, the reason why the laser is used as the light source is that a light beam having less diffusion (i.e. high directivity) is obtained since coherent light is emitted. Besides, the light source section 2 emits the color illumination light having three color components of RGB in this example, but if it is sufficient to acquire a monochrome image, the light source section may be one that emits illumination light for monochrome. Alternatively, it may be one that emits light such as ultraviolet light, infrared light, light for narrow band light observation (NBI: Narrow Band Imaging).

The optical fiber 3 is a light conducting section that guides the illumination light emitted from the light source section 2 and irradiates the light from a distal end to a subject with directivity, and an optical fiber of a single mode type is used for suppressing diffusion of emitted light. The distal end of the optical fiber 3 is arranged at a distal end of the endoscope 6. The irradiated illumination light is reflected by the subject to become return light which enters from a distal end of the optical fiber bundle 9 and the distal end of the optical fiber 3.

The branch optical fiber 4 and the optical coupler 5 are parts of the light conducting section and are branch sections for conducting the return light entered from the distal end of the optical fiber 3 to a position different from the light source section 2. That is, the optical coupler 5 is arranged on a light conducting path by the optical fiber 3 and conducts the illumination light emitted from the light source section 2 to the distal end of the optical fiber 3, but does not conduct the illumination light to a side of the branch optical fiber 4.

Further, the optical coupler 5 conducts the return light entered from the distal end of the optical fiber 3 to the side of the branch optical fiber 4, but does not conduct the return light to a side of the light source section 2.

The endoscope 6 is for being inserted into the subject and the optical fiber 3 and the optical fiber bundle 9 are inserted through the endoscope 6, and the drive element 7 is also disposed.

The drive element 7 and the scanning drive section 8 constitute a scanning section for performing scanning by changing a direction of the distal end of the optical fiber 3. The drive element 7 is a drive source for moving the distal end of the optical fiber and is configured, for example, as a piezoelectric element or the like. Further, the scanning drive section 8 is a driver that controls a driving current to be supplied to the drive element 7.

The optical fiber bundle 9 has the distal end disposed at the end of the endoscope 6, and receives the return light from the subject and conducts the light to a proximal end side. The optical fiber bundle 9 performs light receiving with broad directivity so that light from all directions within a scanning range of the optical fiber 3 can be received.

The first light detection section 11 detects the return light conducted through the optical fiber 3, the optical coupler 5 and the branch optical fiber 4, and thereby detects the light with the same directivity as the distal end of the optical fiber 3.

The second light detection section 12 detects the return light conducted through the optical fiber bundle 9, and thereby detects the light from the scanning range of the distal end of the optical fiber 3 by the drive element 7 and the scanning drive section 8 with directivity broader than that of the first light detection section 11.

The image processing section 15 adds a detection result by the first light detection section 11 and a detection result by the second light detection section 12, and calculates from which direction an addition result indicates a result of detection of the light, based on information about the direction of the distal end of the optical fiber 3 from the scanning drive section 8, and configures an image to be outputted to a monitor 16.

The monitor 16 displays the image configured by the image processing section 15.

Figure 2:
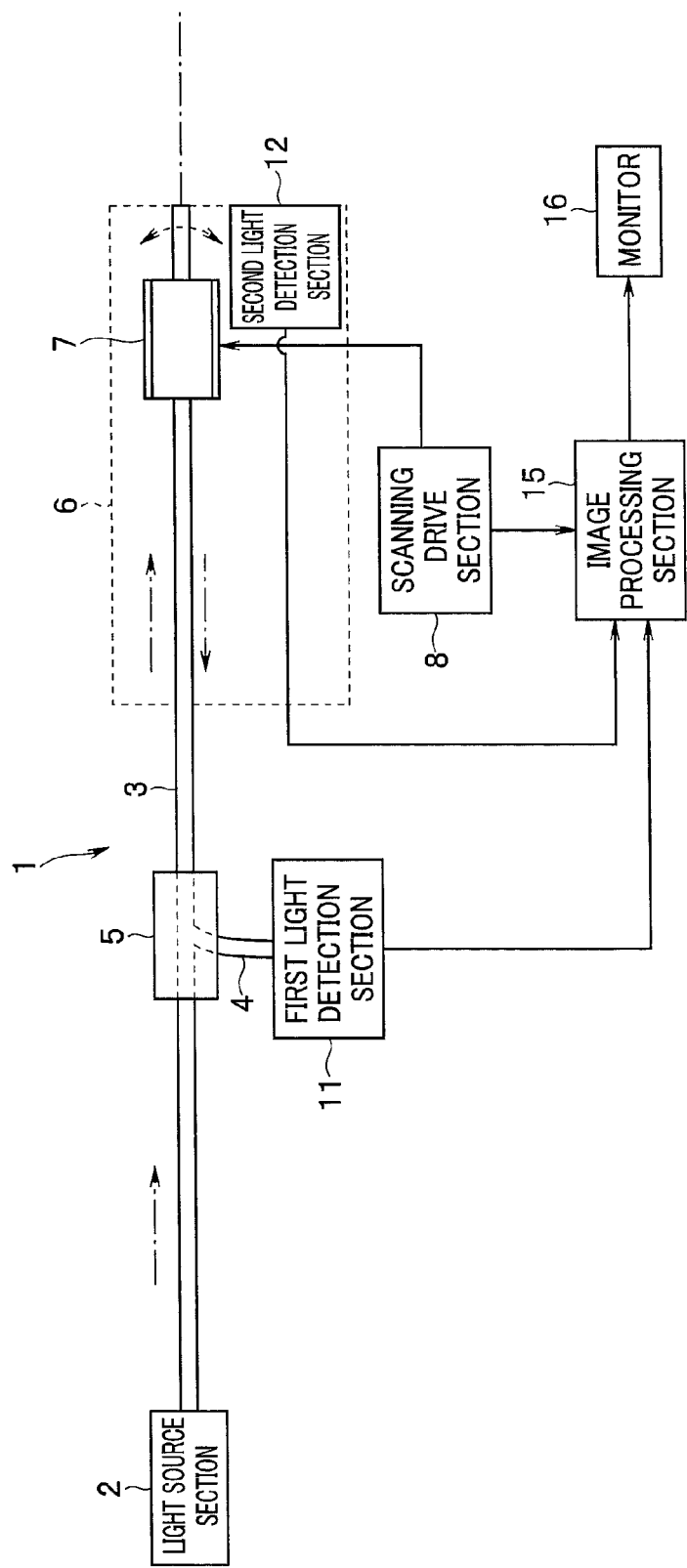
FIG. 2 is a diagram showing a modified example of the configuration of the scanning endoscope apparatus in the embodiment 1.

Moreover, FIG. 2 shows a diagram showing a modified example of the configuration of the scanning endoscope apparatus 1.

In the modified example shown in FIG. 2, the second light detection section 12 is disposed in the vicinity of the distal end of the optical fiber 3 at the distal end portion of the endoscope 6. Therefore, the optical fiber bundle 9 is not provided. The second light detection section 12 performs light receiving with broad directivity so that the light from all directions in the scanning range of the optical fiber 3 can be received in the same manner as described above. If the second light detection section 12 is small in size and light in weight, such configuration may be adopted.

Figure 3:
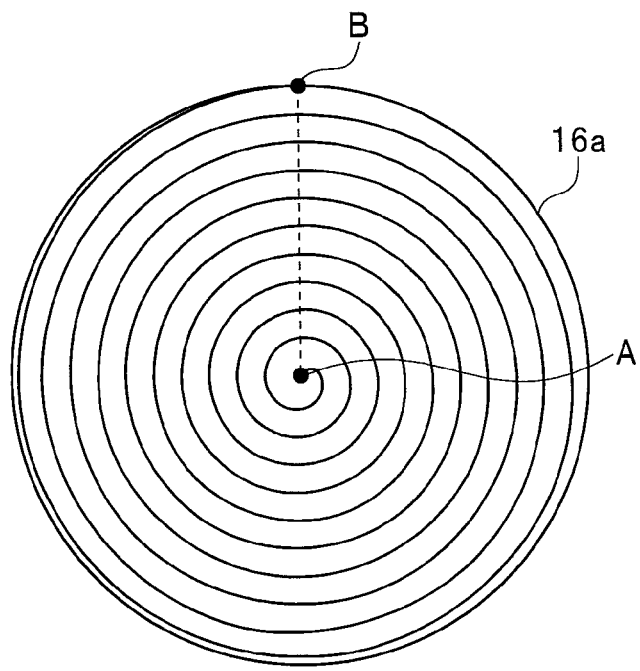
FIG. 3 is a diagram showing a manner of optical light scanning in the scanning endoscope apparatus of the embodiment 1.

Next, FIG. 3 is a diagram showing a manner of optical scanning in the scanning endoscope apparatus 1.

The scanning of the distal end of the optical fiber 3 by the drive element 7 and the scanning drive section 8 is performed, for example, as shown in FIG. 3.

That is, the change of the direction is started from a central point A of an observation filed of view 16a, and the direction of the distal end of the optical fiber 3 is changed along a path of a spiral shape to reach the most distant point B which is furthest from the center. Thereafter, it may be performed such that after the irradiation of the illumination light to the subject is turned off, the direction of the distal end of the optical fiber is returned from the most distant point B to the central point A and the same operation is performed, or the direction of the distal end of the optical fiber is returned in a reverse direction along the spiral path from the most distant point B to the central point A, or alternatively the other method may be adopted. For the convenience of explanation, in the present embodiment, it is assumed that the method of returning along the spiral path in the reverse direction from the most distant point B to the central point A is adopted.

The second light detection section 12 detects the light with the broad directivity so that all the light from the scanning range as shown in FIG. 3 can be received, as described above. Therefore, it can not be determined from which point in the scanning range the light received by the second light detection section 12 has come, solely from the detection result of the second light detection section 12.

Therefore, the image processing section 15 receives information of the direction of the distal end of the optical fiber 3 (i.e. information of an irradiation direction of the illumination light), and presumes that the detection result by the second light detection section 12 concerns the light from the subject in the direction of the distal end of the optical fiber 3, and performs mapping at the position where the detection signal by the second light detection section 12 is presumed, to thereby configure an image.

Figure 4:
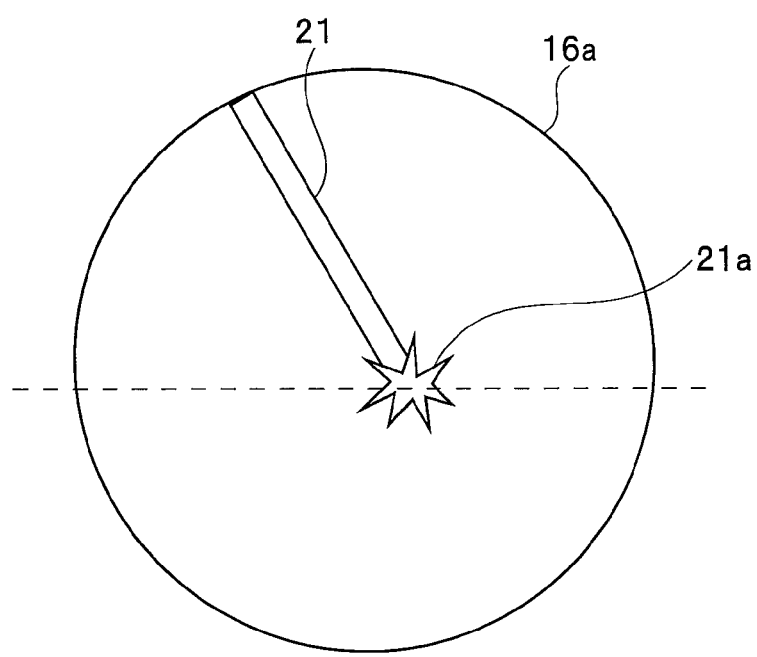
FIG. 4 is a diagram showing a manner in which light generated by a treatment instrument exists within an observation field of view.

Next, FIG. 4 is a diagram showing a manner in which light generated by a treatment instrument 21 exists in an observation field of view 16a.

In an examination by the endoscope 6, there is a case where the treatment instrument 21 is used together. In a case where the treatment instrument 21 is one for performing treatment with light emission to the subject, such as the electric knife and the medical laser, external factor light 21a (which is not the return light of the illumination light emitted from the optical fiber 3) is generated. Further, it is considered that the external factor light 21a is generated with some cause other than the treatment instrument 21.

Figure 5:
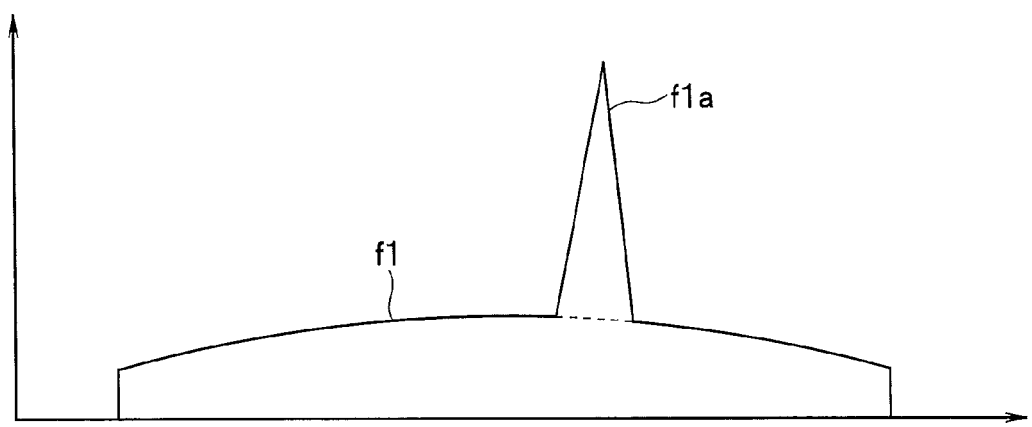
FIG. 5 is a diagram showing an example of a detection result by a first light detection section in the embodiment 1.

A manner of a signal on a line indicated by a dotted line in FIG. 4 obtained in the above case will be explained referring to FIG. 5 and FIG. 6. FIG. 5 is a diagram showing an example of the detection result by the first light detection section 11 and FIG. 6 is a diagram showing an example of the detection result by the second light detection section 12.

First, since the first light detection section 11 detects the light from the direction to which the distal end of the optical fiber 3 is directed, only the return light is detected when the distal end of the optical fiber 3 is not directed to the external factor light 21a. On the other hand, the first light detection section 11 detects the return light and the external factor light 21a when the distal end of the optical fiber 3 is directed to the external factor light 21a. Therefore, a peak f1a corresponding to detection of the external factor light 21a appears in a detection signal f1 of the first light detection section 11.

On the other hand, the second light detection section 12 always detects the external factor light 21a irrespective of the scanning direction of the optical fiber 3 if the external factor light 21a is located within the observation filed of view 16a (i.e. within the scanning range). Therefore, a signal component of the return light of the illumination light from the subject and a signal component f2a of the external factor light 21a are included in a detection signal f2 of the second light detection section 12, and if a luminance level of the external factor light 21a is constant without variation in time, for example, the signal component f2a becomes constant.

Figure 6:
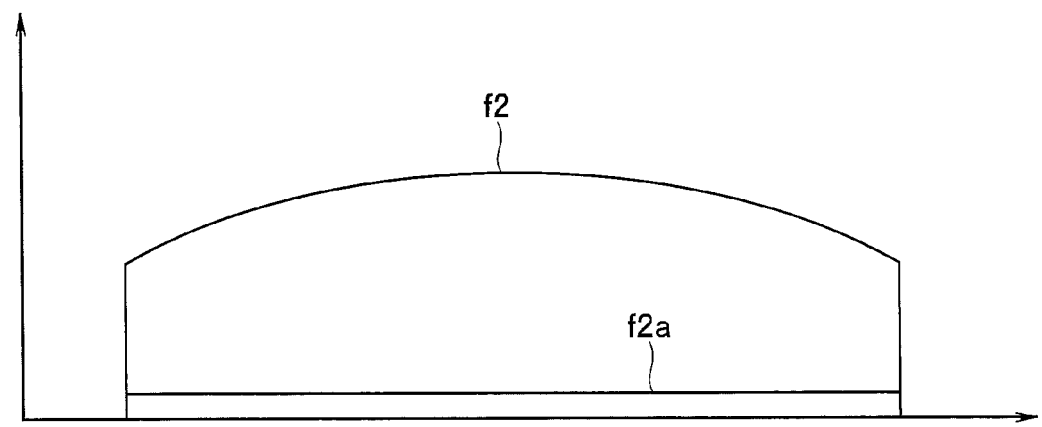
FIG. 6 is a diagram showing an example of a detection result by a second light detection section in the embodiment 1.

Therefore, the image processing section 15 is configured to perform calculation as shown in the following equation 1 based on the detection signal f1 of the first light detection section 11 as shown in FIG. 5 and the detection signal f2 of the second light detection section 12 as shown in FIG. 6, and generates an image signal f.

$$f = \alpha \times f1 + f2 \quad \text{[Equation 1]}$$

where $\alpha$ is a correction coefficient for making signal intensity of the detection signal f1 be consistent with signal intensity of the detection signal f2.

That is, the first light detection section 11 performs the detection through the optical fiber 3 constituted by a single fiber, for example, and the second light detection section 12 performs the detection through the optical fiber bundle 9 constituted by bundling a plurality of fibers. Since a number of fibers can be bundled in the optical fiber bundle 9, it is possible to receive bright light in the second light detection section 12. Further, the optical coupler 5 is provided on a light conducting path of the return light which is detected by the first light detection section 11, but the optical coupler 5 does not exist in a light conducting path of the return light which is detected by the second light detection section 12. Furthermore, it is considered that there is a difference in performance such as variation of an amount of light which is conducted to a side of the branch optical fiber 4 in dependence on what type of product is adopted as the optical coupler 5. In addition, an optical sensor, etc. used in the first light detection section 11 and an optical sensor, etc. used in the second light detection section 12 do not necessarily have the same performance, and it is considered that there is a case where there is a difference in performance in a case of adopting different products, or a case where there is an individual difference in performance even though the same products are adopted. Therefore, it is considered that even if the light from the same part of the subject is received, there is a case where the signal intensity of the detection signal f1 differs from the signal intensity of the detection signal f2, and therefore $\alpha$ is the correction coefficient for correcting such difference. The correction coefficient $\alpha$ is determined to have a predetermined value in accordance with a system configuration of the scanning endoscope apparatus 1 and stored in advance in the image processing section 15.

Figure 7:
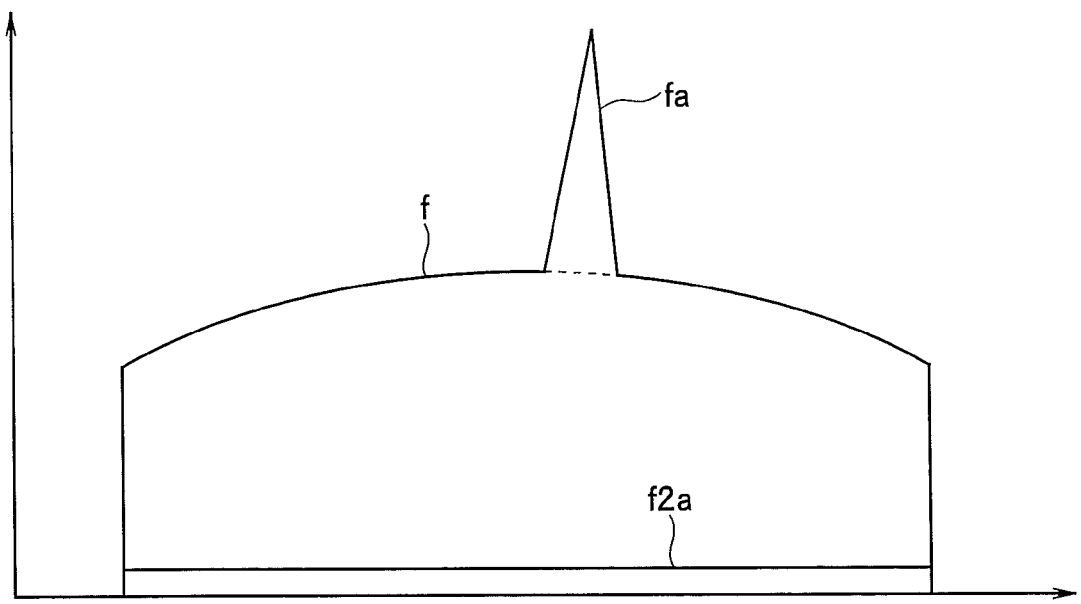
FIG. 7 is a diagram showing a result of addition of the detection result by the first light detection section and the detection result by the second light detection section.

FIG. 7 a diagram showing a result of addition of the detection result by the first light detection section 11 and the detection result by the second light detection section 12.

The image signal f generated by the above-described processing includes the signal component f2a from the second light detection section 12 as a signal component caused by the external factor light 21a and a peak fa corresponding to the peak f1a in the detection signal f1 of the first light detection section 11. Therefore, an image displayed on the monitor 16 on the basis of the image signal f allows observation of a subject image by the return light brightly and also makes it possible to perform observation on at what position in the subject the external factor light 21a is generated.

It is noted that the correction coefficient a is not limited to be fixed to the predetermined value determined in accordance with the system configuration, and it may be configured that a user can vary the correction coefficient $\alpha$ to be desirable. For example, when a value of the correction coefficient $\alpha$ is made larger than the predetermined value, it is made possible to more clearly observe the peak fa caused by the external factor light 21a. On the other hand, when the value of the correction coefficient $\alpha$ is made smaller than the predetermined value, the peak fa caused by the external factor light 21a can be made indistinct, and in particular when the correction coefficient $\alpha$ is set to "0", it is made possible to observe the subject image by the return light without being bothered by the external factor light 21a.

Further, the composition of the image signal f based on the detection signal f1 of the first light detection section 11 and the detection signal f2 of the second light detection section 12 is performed according to equation 1, as described above, but it is not be limited to this method, and a more complicated method may be adopted.

For example, since what is caused by the external factor light 21a is the peak f1a, it may be configured that only the peak f1a is extracted as much as possible and multiplied by α, and thereafter subjected to addition to the detection signal f2 of the second light detection section 12. If the external factor light 21a is generated only within a narrow range in the observation image 16a and influence of the peak f1a on an average value of the detection signal f1 is small, a method of subtracting an average value <f1> of the detection signal f1 from the detection single f1 of the first light detection section 11 is conceived as a relatively easy method of approximately extracting only the peak f1a. In this case, the image signal f can be generated according to the following equation 2 instead of equation 1.

$$f=\alpha\times(f1-<f1>)+f2 \quad \text{[Equation 2]}$$

By subtracting the average value <f1> from the detection signal f1, a return light component included in the detection signal f1 (a gently-sloping signal component except the peak f1a, shown in FIG. 5) is substantially eliminated and almost only the peak f1a remains. Therefore, by generating the image signal f based on the equation 2, it is possible to suppress a raise of a level of the detection result of the second light detection section 12 over the entire image so that contrast of the image can be improved. Moreover, since the return light component is not included in the peak f1a which is extracted by the calculation of (f1−<f1>), by multiplying the peak f1a by the correction coefficient α, it is made possible to precisely reflect a ratio of intensity of the peak f1a which is caused by the external factor light 21a with respect to intensity of the detection signal f2.

According to the above embodiment 1, it is possible to make configuration of an image which allows visual recognition of location of external factor light, and display the image on the monitor 16. Therefore, for example, it is made possible to confirm a region of the subject where the treatment with light emission is performed by the treatment instrument 21.

Further, in the case of performing the processing according to equation 1, it is possible to reduce a processing load and improve real-time processibility since the processing is relatively simple.

On the other hand, in the case of performing the processing according to equation 2, it is possible to improve quality of the image although the processing is relatively simple.

In this case, since the detection result of the first light detection section 11 is multiplied by the correction coefficient α, a light amount ratio between the subject image formed by the return light and the image by the external factor light can be adjusted to be an appropriate ratio. Further, in the case where the correction coefficient α is made variable to have a desired value, it is possible to set whether the image by the external factor light is distinct or indistinct according to user's choice.

Furthermore, since the first light detection section 11 uses the optical fiber 3 itself, which irradiates the illumination light, for receiving the return light, it is possible to completely coincide the irradiation direction of the illumination light with the direction of receiving the light, and also to make it unnecessary to perform an alignment of high precision, etc. in manufacturing.

In addition, in the case of disposing the second light detection section 12 in the vicinity of the distal end of the optical fiber 3, the fiber bundle 9 as shown in FIG. 1 is made unnecessary and only a signal line can be arranged in place of the fiber bundle 9, and therefore there is an advantage of making it possible to attempt reduction of a diameter of the endoscope 6.

[Embodiment 2]

Figure 8:
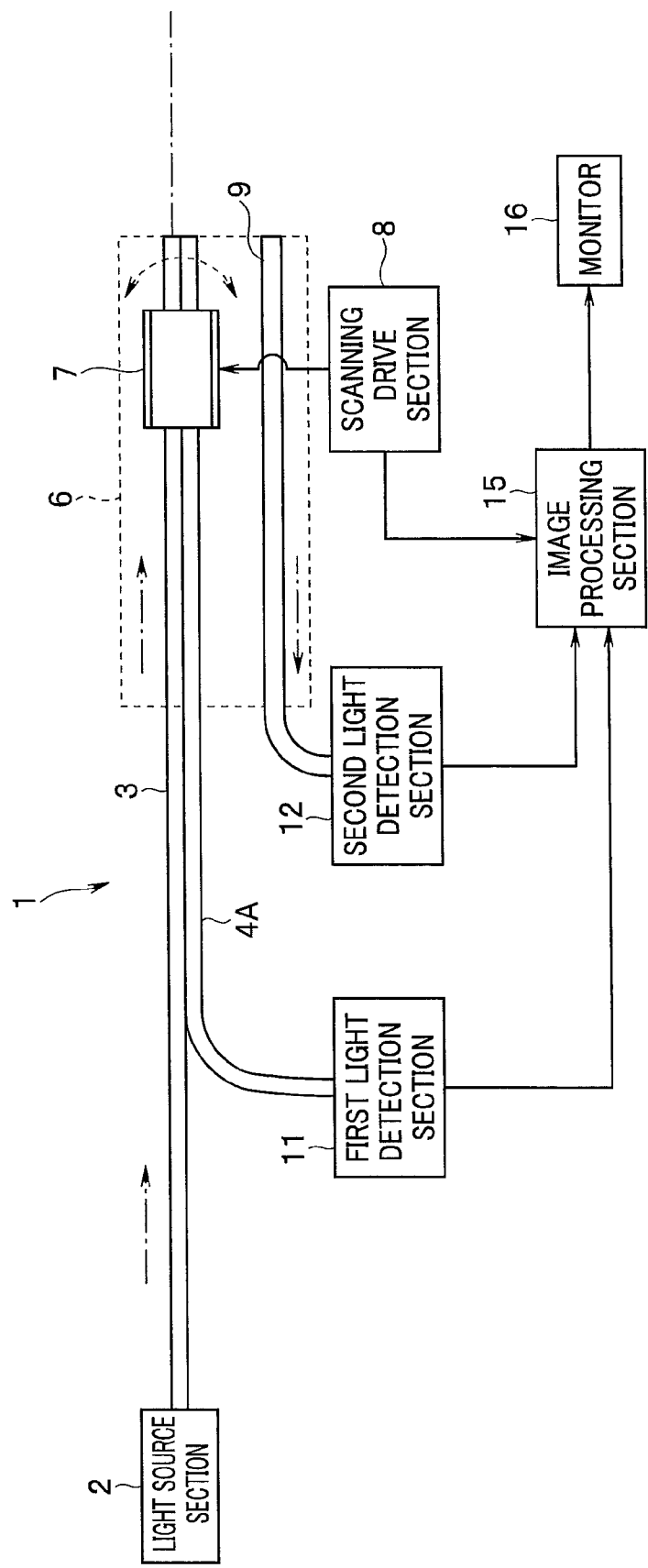
FIG. 8 is a diagram showing a configuration example of the scanning endoscope apparatus in embodiment 2 of the present invention.

FIG. 8 shows embodiment 2 of the present invention, and is a diagram showing a configuration example of a scanning endoscope apparatus. In the embodiment 2, description will be appropriately omitted by assigning the same reference signs to parts similar to those in the embodiment 1, etc. and only the different points will be explained.

The scanning endoscope apparatus 1 of the present embodiment is configured by providing a second optical fiber 4A, which is a second light conducting section, instead of the optical coupler 5 and the branch optical fiber 4.

The second optical fiber 4A is disposed along the optical fiber 3 integrally therewith in the endoscope 6, and in particular a distal end thereof is integrated so as to be directed to the same direction as the distal end of the optical fiber 3.

Further, the second optical fiber 4A performs scanning by the drive element 7 and the scanning drive section 8, to have the same directivity as the distal end of the optical fiber 3, integrally therewith.

As a result, the first light detection section 11 detects light conducted through the second optical fiber 4A to thereby detect the light with the same directivity as the distal end of the optical fiber 3.

Besides, in the configuration of the present embodiment also, the second light detection section 12 may be disposed in the vicinity of the distal end of the optical fiber 3 at the distal end portion of the endoscope 6, as a matter of course.

By adopting the configuration of the above embodiment 2, substantially the same effect as the embodiment 1 described above can be achieved and there is an advantage that an optical member such as the optical coupler 5 is made unnecessary.

It is noted that the present invention is not limited to the above-described embodiments just as they are, and can be embodied by modifying the elements within a range not to deviate from the gist of the invention at a stage of carrying out the invention. Further, various aspects of the invention can be formed by appropriate combination of the plurality of elements disclosed in the above embodiments. For example, some elements may be omitted in all the elements shown in the embodiments. Further, the elements in the different embodiments may be combined appropriately. Thus, it is a matter of course that various modifications and applications are possible within the range not to deviate from the gist of the invention.

What is claimed is:

1. A scanning endoscope apparatus comprising:
   a light source section that emits illumination light;
   a light conducting section that conducts the illumination light and irradiates the illumination light from a distal end to a subject with directivity;
   a scanning section that performs scanning by changing a direction of the distal end of the light conducting section;
   a first light detection section that generates a signal by detecting only light from a direction in which the distal end of the light conducting section is oriented which is scanned by the scanning section;
   a second light detection section that generates a signal by detecting light from a scanning range of the distal end of the light conducting section by the scanning section with directivity which is broader than directivity of the first light detection section;

an image processing section that performs processing of adding the signal generated by the first light detection section and the signal generated by the second light detection section, and forms image information to be outputted to a display section, which displays an image, based on a result of the addition processing.

2. The scanning endoscope apparatus according to claim 1, wherein the light conducting section comprises a branch section that conducts light entered from the distal end of the light conducting section to a position different from a position of the light source section, and the first light detection section detects the light conducted through the branch section to thereby detect the light with the same directivity as the distal end of the light conducting section.

3. The scanning endoscope apparatus according to claim 1, further comprising:

a second light conducting section that has a distal end configured to perform scanning by the scanning section integrally with the distal end of the light conducting section with the same directivity as the distal end of the light conducting section, wherein the first light detection section detects light conducted through the second light conducting section to thereby detect the light with the same directivity as the distal end of the light conducting section.

4. The scanning endoscope apparatus according to claim 1, wherein the image processing section multiplies the detection result by the first light detection section by a correction coefficient and then performs addition to the detection result by the second light detection section.

5. The scanning endoscope apparatus according to claim 1, wherein the second light detection section is disposed in a vicinity of the distal end of the light conducting section.

* * * * *